United States Patent [19]

Quang et al.

[11] Patent Number: 5,045,096
[45] Date of Patent: Sep. 3, 1991

[54] DEVICES FOR DE-AERATING LIQUIDS FLOWING IN MEDICAL LIQUID SYSTEMS

[76] Inventors: Minh B. Quang, Rathausmarkt 2d, 2406 Stockelsdorf; Eberhard Frank, W',uml/o/ rth Weg 18, 7910 Neu-Ulm 8, both of Fed. Rep. of Germany

[21] Appl. No.: 408,882

[22] Filed: Sep. 18, 1989

[30] Foreign Application Priority Data

Sep. 21, 1988 [DE] Fed. Rep. of Germany ....... 3832028

[51] Int. Cl.⁵ .............................................. B01D 19/00
[52] U.S. Cl. ........................................ 55/159; 55/321; 210/436; 604/126
[58] Field of Search .................. 55/159, 321; 210/188, 210/436; 604/126, 406

[56] References Cited

U.S. PATENT DOCUMENTS

| | | |
|---|---|---|
| 3,593,854 | 7/1971 | Swank ................... 210/436 |
| 3,650,093 | 3/1972 | Rosenberg ............. 55/159 |
| 3,803,810 | 4/1974 | Rosenberg ............. 55/159 |
| 3,834,124 | 9/1974 | Ichikawa ............... 55/159 |
| 4,568,366 | 2/1986 | Frederick et al. ..... 55/159 |
| 4,615,694 | 10/1986 | Raines .................. 604/126 |

*Primary Examiner*—Charles Hart
*Attorney, Agent, or Firm*—Dvorak and Traub

[57] ABSTRACT

A device for de-aerating liquids flowing in medical liquid systems and in particular infusible liquids to be administered from a gravity-operated infusion set, comprises a hollow chamber through which the infusible solution flows and whose wall contains at least one aperture in which is inserted a liquid-tight, air-permeable de-aerating unit. By means of the device, air bubbles can be removed automatically from infusible solutions being administered.

15 Claims, 1 Drawing Sheet

DEVICES FOR DE-AERATING LIQUIDS FLOWING IN MEDICAL LIQUID SYSTEMS

BACKGROUND OF THE INVENTION

1. Field of the Invention

The invention relates to a device for de-aerating liquids flowing in medical liquid systems and in particular infusible solutions to be administered from a gravity-operated infusion set.

2. Description of the Prior Art

When an infusion set is being connected up to an infusion bottle or when infusion bottles are being changed, or when a number of medical liquid systems are being coupled together, in practice it often happens that air may get into the lines carrying the infusible solutions, particularly when they are flexible tubes. Before the infusion begins all the air has to be removed from the lines. This is done by uncoupling the infusion set from the patient. The process of uncoupling to get rid of the air takes time. To ensure the safety of the patient when he or she is undergoing infusion therapy, the uncoupling to get rid of the air has to be carried out with the greatest of care, thus increasing still further the time taken.

The main object of the present invention is to provide a device by means of which air inclusions can be removed automatically from infusible solutions being administered.

SUMMARY OF THE INVENTION

To this end, the present invention consists in a device for de-aerating liquids flowing in medical liquid systems, said device being characterized by a hollow chamber through which the infusible solution flows, whose wall contains at least one aperture in which is inserted a liquid-tight, air-permeable de-aerating unit.

The device according to the invention may advantageously be inserted into the tubing system of an infusion set. Relative to the direction of flow, it is helpful for the device to be inserted into a line carrying an infusible solution, upstream of the flow controller, e.g. a roller clamp, of the infusion set. The infusible solution fed in from an infusion bottle flows into the hollow chamber. Air bubbles entrained in it collect in the hollow chamber. The quantity of air which collects can then leave the hollow chamber directly through the liquid-tight but air-permeable de-aerating unit which is inserted in an aperture in the hollow chamber. The infusible solution will then be free of bubbles when it flows out of the hollow chamber.

Since the free cross-section of the interior of the hollow chamber is larger than that of the flexible tube feeding it, the rate of flow of the infusible solution fed into the hollow chamber will be reduced in the chamber. The flow of infusible solution which is smoothed in this way, combined with the hydrodynamically generated rise in pressure, causes the entrained air bubbles to be ideally separated from the liquid contained in the hollow chamber and to be expelled from the chamber through one or more de-aerating units.

In a refinement of the invention, the hollow chamber is cup-shaped in configuration and at the ends is provided with connecting sections, with a first connecting section containing an outlet passage running from the interior of the hollow chamber and a second connecting section containing an inlet passage which opens into the hollow chamber. The hollow chamber with the connecting sections at its two ends is a component of simple design which can be produced at relatively low cost. The cup-shaped hollow chamber is simply closed off at the two ends by the respective connecting sections. It is possible for simple connecting elements to be added or molded on at the outlet and inlet passages in the respective connecting sections, these elements allowing plugging in or connection to flexible outlet and inlet tubes respectively for infusible solutions. Also, any infusion set already in use in a clinic can be retrofitted in an advantageously simple fashion with the de-aerating device according to the invention simply by cutting a flexible tube.

In a further refinement of the invention, the opening of the inlet passage into the hollow chamber is orientated transversely to the longitudinal axis of the chamber. An orientation of this kind for the opening of the inlet passage has the advantage that a de-aerating unit positioned in the wall of the cup-shaped hollow chamber is situated in the immediate vicinity of the opening, and the liquid which flows out of the opening and into the hollow chamber may, with advantage, be aimed directly at the de-aerating unit situated opposite. Air bubbles contained in the liquid entering the chamber thus follow a very short route direct to the de-aerating unit and are quickly separated out of the liquid.

In this case, it is advantageous for the arrangement to be such that the free cross-section of the opening is smaller than the cross-section of the inlet passage. The rate of flow of the liquid flowing in the inlet passage is first of all raised in the small opening. At the transition from the small opening into the far larger chamber, there is a considerable slowing down of the rate of flow and thus an increase in pressure in the chamber. This hydrodynamic effect is increased still further by the small cross-section of the inlet passage into the hollow chamber. The above-atmospheric pressure which is thus generated in the hollow chamber causes the air to be swiftly expelled from the chamber and also prevents any ambient air from being drawn into the chamber through the de-aerating unit by suction.

The device is also notable for the fact that an end portion of the inlet passage, which contains the opening, projects into the hollow chamber. This creates between the end portion projecting into the hollow chamber and the inner wall of the chamber an annular space in which air bubbles present in the incoming liquid can collect and then travel by a very short route to a de-aerating unit which, being positioned in the wall of the hollow chamber, can with advantage be placed more directly opposite the opening of the inlet passage which is arranged in the outer periphery of the end portion. In addition, the inner periphery of the hollow chamber may advantageously be orientated parallel to the outer periphery of the end portion of the inlet passage. What is more, the air releasing effect may be further increased by making the outer periphery of the end portion of the inlet passage conical in shape. Since the inner periphery of the hollow chamber is arranged in parallel, it too will be conical, and there will thus be, in the conical annular space between the inner periphery of the hollow chamber and the outer periphery of the inlet passage, a conical collecting space which is more effective in collecting the air bubbles. The rise in pressure in the hollow chamber which was described above then expels the air inclusions, once they reach the annular collecting space in the hollow chamber, through the de-aerating units.

In the device according to the invention, it is particularly advantageous for a liquid filter also to be positioned in the interior of the hollow chamber in front of the opening at the entry to the outlet passage. The first advantage which the liquid filter has is that it traps foreign particles which are present, given that the infusible solution being administered is forced to flow through it before it leaves the hollow chamber, free of bubbles and foreign particles, through the outlet passage in the first connecting section, from where it flows along a flexible tube to the patient. A further advantage which the liquid filter has is that, due to its resistance to flow, it slows down the flow of the liquid in the hollow chamber by a specific amount, which likewise causes a corresponding rise in pressure in the chamber and boosts the air-releasing action.

Each de-aerating unit preferably comprises a filter holder, inserted in the associated aperture, whose free cross-section is blanked off by at least one filtering layer arranged in the filter. It is advantageous for the filtering layer to be a hydrophobic, bacteria-tight membrane filter. A preferred material suitable for a filter of this kind is polytetrafluoroethylene (PTFE). The filter layer may also comprise a hydrophobic, fine pored material and a second, bacteria-tight air filtering stratum. A cellulose nitrate filter or a cellulose acetate filter is a suitable material for the air filtering stratum. The liquid filter for filtering foreign particles out of the infusible solution may for example have a mesh size of approx. 15 μm and may be made of polyamide fibres. A liquid filter of this kind is suitable for trapping most foreign particles. It is particularly advantageous for the resistance of a liquid filter of this kind to be higher than the resistance to air of the filter layers which release the air, especially when the liquid filter is wetted by the liquid.

The device, i.e. the hollow chamber, plus the connecting sections, is preferably produced from transparent plastic material, a particularly simple design being notable for the fact that a first tubing connecting section which contains the outlet passage is in the form of an end-wall to the hollow chamber and a second tubing connecting section which contains the inlet passage is in the form of a cover which closes off the hollow chamber. The connecting sections situated at the ends of the hollow chamber act as simple plug-in connectors for fitting flexible tubing through which the infusible solution can be fed in and out. To assemble the device from its individual components, the liquid filter is first fitted in the hollow chamber. If the tubing connecting section which contains the outlet passage is molded onto the hollow chamber, the latter then only needs to be closed off by the second connecting section containing the inlet passage. For this purpose the second tubing connecting section may for example be bonded to the hollow chamber. It is however equally possible for both the tubing connecting sections to be bonded to the hollow chamber to close it off, once the liquid filter has been fitted in it. After this the apertures in the walls of the hollow chamber can be fitted with the appropriate de-aerating units by fitting the de-aerating filters.

BRIEF DESCRIPTION OF THE DRAWINGS

In order that the invention may be more readily understood, some embodiments thereof will now be described, by way of example, with reference to the accompanying drawings, in which.

DESCRIPTION OF THE PREFERRED EMBODIMENTS

Figure 1:
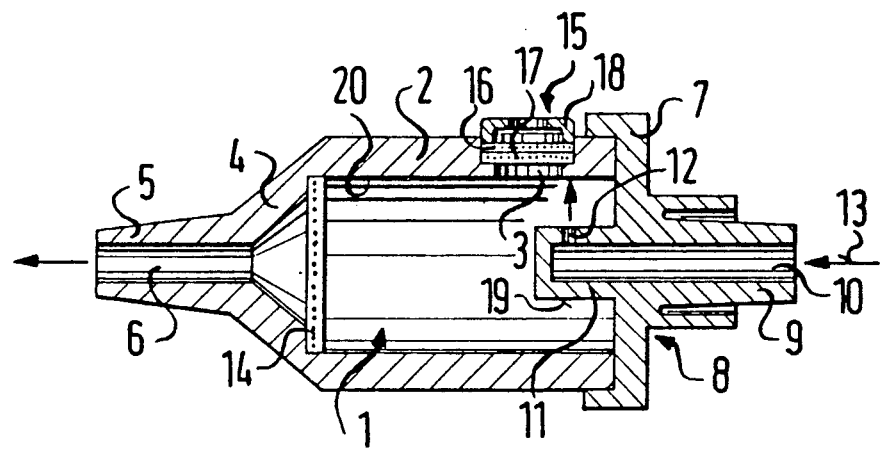
FIG. 1 is a side elevation in longitudinal section of a first embodiment of a device for de-aerating infusible liquids flowing in medical liquid systems.

Referring to FIG. 1 of the drawings, the illustrated device for de-aerating infusible solutions comprises a hollow chamber 1 of cup-shaped configuration and having at least one aperture 3 in its cylindrical wall 2. One end of the cup-shaped hollow chamber is closed off by forming it into a first connecting section 4 which extends into a tubing connector 5 and which contains an outlet passage 6 running from the interior of the hollow chamber 1. A tube to carry away infusible solutions for example can be plugged onto the tubing connector 5.

The opposing open end of the hollow chamber 1 is closed off by a second connecting section 8 having a cover 7, with a tubing connector 9 which contains an inlet passage 10 leading into the hollow chamber. An end portion 11 of the inlet passage projects into the hollow chamber like a head. An opening 12 from the inlet passage is orientated transversely to the longitudinal axis of the hollow chamber, thus being situated approximately opposite the aperture 3 in the wall 2 of the cup-shaped hollow chamber 1. Liquid flowing through the inlet passage in the direction of arrow 13, e.g. infusible solution, enters the hollow chamber 1 through the opening 12. As the liquid flows through from the small opening 12 into the many times larger chamber 1 there is, under the laws of flow mechanics, a slowing down in its rate of flow and thus an increase in pressure in the chamber 1. Inserted into the chamber in front of the outlet passage 6 is a liquid filter 14 which serves to filter foreign particles out of the liquid fed to it. The resistance presented by the liquid filter 14 similarly decelerates the flow of liquid by a specific amount, thus creating a further rise in pressure in the chamber 1. Fitted in the aperture 3 situated in the wall of the hollow chamber 1 is a liquid-tight, air-permeable de-aerating unit 15, which in the present embodiment has a filter layer comprising a bacteria-tight air filtering stratum 16, made of cellulose nitrate or cellulose acetate for example, and a filter stratum 17 made from a fine-pored hydrophobic material such a PTFE for example. Reference numeral 18 identifies the filter holder which fixes strata 16 and 17 in position.

Figure 2:
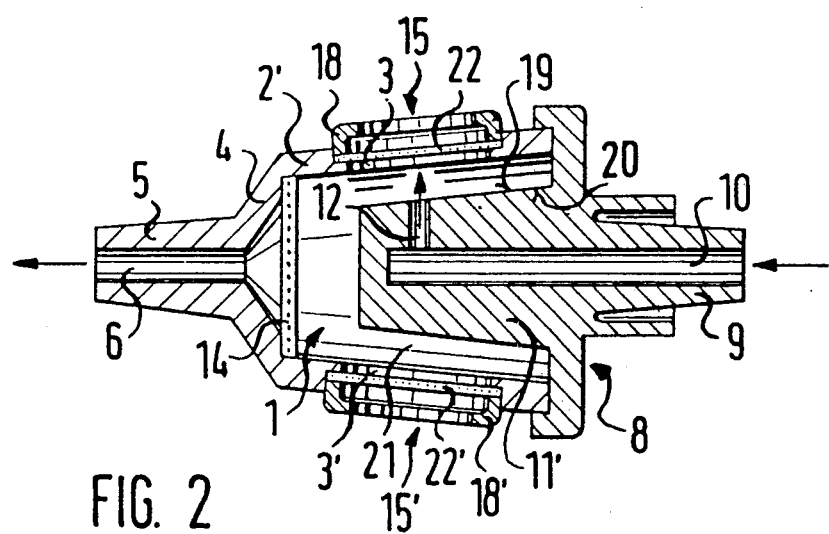
FIG. 2 is a side elevation in longitudinal section of a second embodiment of the device.

FIG. 2 shows a second embodiment of the device, once again in side elevation and longitudinal section. The same components bear the same reference numerals. In this embodiment the end portion 11' of the connecting section 8 which contains the inlet passage 10 has a conical outer periphery 19. The opposing inner periphery 20 of the wall 2' of the hollow chamber 1 extends parallel to the outer periphery 19, thus creating an annular space, of conical configuration likewise, between the end portion and the inner periphery 20 of the hollow chamber. Air bubbles needing to be separated from the incoming liquid can collect in this annular chamber in the ideal fashion. Arranged in the wall 2' are a plurality of apertures 3,3' in which are inserted de-aerating units 15, 15' in this embodiment which comprise a hydrophobic, bacteria-tight membrane filter 22,22'. The hydrophobic bacteria-tight membrane filters may for example be composed of polytetrafluoroethylene (PTFE). Numerals 18,18' again refer to filter holders.

It will be appreciated that the invention is not limited to the embodiments herein described but includes all modifications and variations falling within its scope.

We claim:

1. A device for de-aerating liquids flowing in medical liquid systems, in particular infusible solutions to be administered from a gravity-operated infusion set, said device comprising a hollow chamber through which the infusible solution flows, said chamber having a wall containing at least one aperture in which a liquid-tight air-permeable de-aerating unit is fitted, wherein the hollow chamber is cup-shaped in configuration and at the ends is provided with connecting sections with a first connecting section having an outlet passage running from the interior of the hollow chamber and a second connecting section having an inlet passage which opens into the hollow chamber, and wherein an outlet orifice from the inlet passage into the hollow chamber is orientated transversely to the longitudinal axis of the hollow chamber and leads the flow directly to the de-aerating unit.

2. A device according to claim 1, wherein the free cross-section of the opening is smaller than the cross-section of the inlet passage.

3. A device according to claim 1, wherein an end portion of the inlet passage which projects into the hollow chamber contains the opening from the inlet passage into the hollow chamber.

4. A device according to claim 1, wherein the inner periphery of the hollow chamber is orientated parallel to the outer periphery of the end portion of the inlet passage.

5. A device according to claim 4, wherein the outer periphery of the end portion of the inlet passage is conical.

6. A device according to claim 1, wherein a liquid filter is positioned in the interior of the hollow chamber in front of the opening into the outlet passage.

7. A device according to claim 1, wherein each de-aerating unit comprises a filter holder inserted in the associated aperture, whose free cross-section is blanked off by at least one filter layer positioned in the filter holder.

8. A device according to claim 7, wherein the filter layer (22,22') is a hydrophobic, anti-bacterial membrane filter.

9. A device according to claim 8, wherein the material for the filter layer is polytetrafluoroethylene.

10. A device according to claim 7, wherein the filter layer comprises a fine-pored hydrophobic stratum and a bacteria-tight air-filtering stratum.

11. A device according to claim 10, wherein the material for the fine-pored hydrophobic stratum is polytetrafluoroethylene.

12. A device according to claim 10, wherein the air filtering stratum is a cellulose nitrate filter or a cellulose acetate filter.

13. A device according to claim 1, wherein the first connecting section which contains the outlet passage is in the form of a tubing connector and forms an end-wall of the hollow chamber, and the second connecting section which contains the inlet passage is in the form of a tubing connector and provides a cover which closes off the hollow chamber.

14. A device according to claim 13, wherein at least one of the connecting sections is bonded to the hollow chamber.

15. A device according to claim 1, wherein the hollow chamber and the connecting sections are injection moldings made from a transparent plastics material.

* * * * *